United States Patent
Ogawa et al.

(10) Patent No.: US 8,039,548 B2
(45) Date of Patent: Oct. 18, 2011

(54) METHOD FOR PURIFYING HYDROXYCARBOXYLIC ACID, METHOD FOR PRODUCING CYCLIC ESTER, AND METHOD FOR PRODUCING POLYHYDROXYCARBOXYLIC ACID

(75) Inventors: Tomoyuki Ogawa, Fukushima-Ken (JP); Michio Kikuchi, Fukushima-Ken (JP)

(73) Assignee: Kureha Corporation, Tokyo (JP)

( * ) Notice: Subject to any disclaimer, the term of this patent is extended or adjusted under 35 U.S.C. 154(b) by 300 days.

(21) Appl. No.: 12/309,872

(22) PCT Filed: Jul. 10, 2007

(86) PCT No.: PCT/JP2007/063751
§ 371 (c)(1),
(2), (4) Date: Feb. 2, 2009

(87) PCT Pub. No.: WO2008/015885
PCT Pub. Date: Feb. 7, 2008

(65) Prior Publication Data
US 2009/0318716 A1   Dec. 24, 2009

(30) Foreign Application Priority Data

Aug. 2, 2006 (JP) ................. 2006-211247
Feb. 5, 2007 (JP) ................. 2007-025282

(51) Int. Cl.
C08G 63/06 (2006.01)
C08G 73/10 (2006.01)
C07D 307/00 (2006.01)
C07C 59/00 (2006.01)
C07C 51/42 (2006.01)

(52) U.S. Cl. ........ 524/600; 528/361; 549/326; 562/579; 562/580

(58) Field of Classification Search ............. 549/326; 562/579, 580; 524/600; 528/361
See application file for complete search history.

(56) References Cited

U.S. PATENT DOCUMENTS

| 2004/0122240 A1 | 6/2004 | Yamane et al. |
| 2005/0020853 A1 | 1/2005 | Kuroda et al. |
| 2007/0015936 A1 | 1/2007 | Meng et al. |

FOREIGN PATENT DOCUMENTS

| EP | 1 232 137 | 7/2005 |
| WO | 02/083661 | 10/2002 |

OTHER PUBLICATIONS

Supplementary European Search Report issued Aug. 24, 2010 in European Patent Application No. 07 79 0569.
International Search Report issued in the International (PCT) Application of which the present application is the U.S. National Stage, Sep. 2007.

*Primary Examiner* — Taylor Victor Oh
(74) *Attorney, Agent, or Firm* — Wenderoth, Lind & Ponack, L.L.P.

(57) ABSTRACT

A process for purification of a hydroxycarboxylic acid by distillation, comprising: distilling a hydroxycarboxylic acid solution containing a high-boiling point hydroxy compound comprising at least one species selected from the group consisting of alcohols and phenols having a higher boiling point than the hydroxycarboxylic acid. As a result, a hydroxycarboxylic acid suitable as a starting material for production of a polyhydroxycarboxylic acid can be obtained. The purified hydroxycarboxylic acid is further polycondensed to provide a hydroxycarboxylic acid oligomer, which is de-polymerized to provide a cyclic ester comprising a dimer of the hydroxycarboxylic acid, and the cyclic ester is converted into a polyhydroxycarboxylic acid by ring-opening polymerization thereof.

6 Claims, 1 Drawing Sheet

US 8,039,548 B2

METHOD FOR PURIFYING HYDROXYCARBOXYLIC ACID, METHOD FOR PRODUCING CYCLIC ESTER, AND METHOD FOR PRODUCING POLYHYDROXYCARBOXYLIC ACID

TECHNICAL FIELD

The present invention relates to a process for purifying or refining a hydroxycarboxylic acid suitable as a starting material for production of a polyhydroxycarboxylic acid, a process for producing a cyclic ester including the purification or refining process and a process for producing a polyhydroxycarboxylic acid.

BACKGROUND ART

Polyhydroxycarboxylic acids (aliphatic polyesters), such as polyglycolic acid and polylactic acid, can be degraded or decomposed by microorganisms or enzymes present in natural environments including soils and sea waters and are accordingly noted as biodegradable polymer materials exerting little load to the environments. Further, as polyhydroxycarboxylic acids are degradable and absorbable in vivo, they are also used as polymeric materials for medical use, such as surgical sutures and artificial skins.

Among the polyhydroxycarboxylic acids, polyglycolic acid is excellent in gas-barrier properties inclusive of oxygen gas-barrier property, carbon dioxide gas-barrier property and water vapor barrier property and also excellent in heat resistance and mechanical strength, so that the development for various use thereof as a single material or in a composite form together with another resin material is undertaken in the fields of packaging materials, etc.

A polyhydroxycarboxylic acid can be synthesized by dehydro-polycondensation of a hydroxycarboxylic acid, such as glycolic acid (hydroxyacetic acid) or lactic acid (hydroxypropanoic acid), whereas in order to effectively produce a high-molecular weight aliphatic polyester, there has been generally adopted a process of synthesizing a bimolecular cyclic ester of the hydroxycarboxylic acid and subjecting the cyclic ester to ring-opening polymerization. For example, the ring-opening polymerization of glycolide (i.e., bimolecular cyclic ester of glycolic acid) provides polyglycolic acid, and the ring-opening polymerization of lactide (i.e., bimolecular cyclic ester of lactic acid) provides polylactic acid.

In any case, as a starting material for a polyhydroxycarboxylic acid with a high molecular weight and little abnormal linkage content, a hydroxycarboxylic acid is required to have a high purity to some extent, but an industrially available hydroxycarboxylic acid is inevitably accompanied with impurities actually. For example, glycolic acid obtained by carbonylation of formaldehyde in water, in the presence of an organic acid and sulfuric acid as catalysts, contains glycolic acid dimer or oligomer formed by ester-forming dehydrocondensation of glycolic acid and di-glycolic acid ($OCCH_2COOH)_2$) that is a dimer formed by ether-forming dehydrocondensation of glycolic acid as major impurities in addition to residues of the catalysts. Then, minor components such as the catalyst residues and ionic impurities can be easily separated and removed industrially by such means as adsorption or ion exchange, but a separate means is required for removal of organic impurities. For example, Patent document 1 listed below describes that a 70% industrial-grade glycolic acid aqueous solution typically shows the following composition:

| | |
|---|---|
| glycolic acid | 62.4 wt. % |
| glycolic acid dimer | 8.8 wt. % |
| di-glycolic acid | 2.2 wt. % |
| methoxyacetic acid | 2.2 wt. % |
| formic acid | 0.24 wt. %. |

As general methods for purification or refining by separation of organic materials, unit operations, such as distillation and crystallization, are known. The application of such a purification or refining method to purification of a hydroxycarboxylic acid is, however, accompanied with an inherent difficulty that a hydroxycarboxylic acid readily causes polycondensation under heating. In view of this, distillation involving heating as an essential factor has been considered basically difficult to be adopted, and the purification has been conventionally performed principally by way of crystallization (Patent documents 1-3 listed below). The purification of a hydroxycarboxylic acid by crystallization is generally performed by cooling of an aqueous solution. However, as the solubility of a hydroxycarboxylic acid, particularly glycolic acid and lactic acid, in water is very high, the cooling is required down to 10° C. or below at the minimum or down to below the ice point for recovering the crystal at a high yield, thus requiring a large-scale refrigeration system. Further, the purity of the crystal depends on the operation of solid-liquid separation, so that a large-scale solid-liquid separation apparatus, such as a centrifuge. Thus, the purification by crystallization involves a difficulty that a large-scale apparatus and a high running cost are required, thus resulting in a high purification cost.

With respect to lactic acid having a lower thermal polycondensability than glycolic acid, there has been proposed a method of performing the distillation while replenishing water in order to keep a low concentration of the lactic acid in the aqueous solution thereof (Patent document 4 below). However, this distillation method for purification of hydroxycarboxylic acid is accompanied with an energy loss due to distillation of a large volume of water which has a lower boiling point and a higher vaporizability than hydroxycarboxylic acid and also an increased cost for recovering the hydroxycarboxylic acid by way of condensation of the resultant hydroxycarboxylic acid aqueous solution, thus also involving a problem regarding the purification cost.

Patent document 1: JP-A 6-501268
Patent document 2: WO2003/064366
Patent document 3: JP-A 2006-169185
Patent document 4: JP-A 2002-128727

DISCLOSURE OF INVENTION

Accordingly, a principal object of the present invention is to provide an industrially feasible process for purifying a hydroxycarboxylic acid as a starting material for production of a polyhydroxycarboxylic acid, a process for producing a cyclic ester including the purification process and a process for producing a polyhydroxycarboxylic acid.

As a result of our study with the above object and repetition of various experiments, we have had a knowledge that it is possible to efficiently perform the purification or refining for providing a purity of hydroxycarboxylic acid at a level useful as a starting material for production of polyhydroxycarboxylic acid by distillation of a hydroxycarboxylic acid solution containing a high-boiling point hydroxyl compound comprising at least one species selected from the group consisting of alcohols and phenols. Thus, the process for purification of a hydroxycarboxylic acid according to the present invention is characterized by comprising: distilling a hydroxycarboxylic acid solution containing a high-boiling point hydroxy compound comprising at least one species selected from the group consisting of alcohols and phenols having a higher boiling point than hydroxycarboxylic acid. In the above-mentioned process, the high-boiling point hydroxy compound per se is not distilled but remains in the distillation mother liquid (which is used herein to mean the whole liquid remaining actually in the distillation apparatus and being heated for the distillation), thereby functioning to suppress the polycondensation of the hydroxycarboxylic acid and allow the continuation of the heating of the mother liquid for the distillation.

Further, the process for producing a cyclic ester according to the present invention is characterized by comprising: polycondensing a hydroxycarboxylic acid purified through the above-mentioned process to form an oligomer thereof, and then de-polymerizing the oligomer in mixture with a polar organic solvent to obtain a dimer cyclic ester. This is based on a knowledge that the above-mentioned process for purifying a hydroxycarboxylic acid is effective for reducing an ether-type hydroxycarboxylic acid dimer (e.g., diglycolic acid) functioning as an impurity obstructing the de-polymerization of the oligomer in the above-mentioned cyclic ester production process.

Further, the process for producing a polyhydroxycarboxylic acid according to the present invention is characterized by comprising: subjecting the cyclic ester thus produced to ring-opening polymerization.

BEST MODE FOR PRACTICING THE INVENTION

Figure 1:
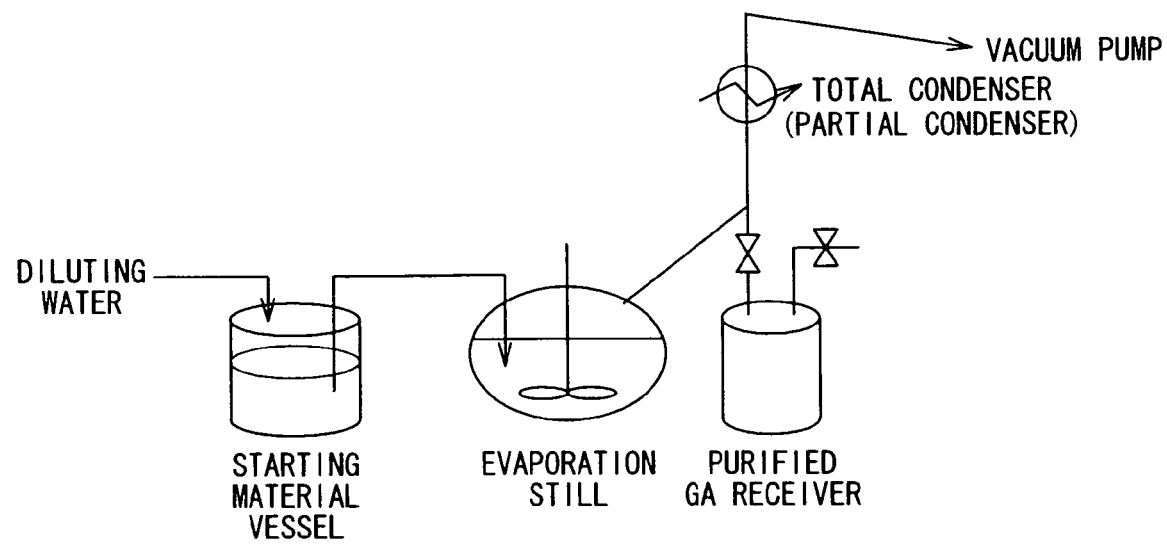
FIG. 1 is a schematic illustration of an apparatus system used in Example (and Comparative Example) of the process for purifying a hydroxycarboxylic acid according to the present invention.

The hydroxycarboxylic acid processed according to the present invention is preferably an α-hydroxycarboxylic acid having a relatively low boiling point, such as glycolic acid, lactic acid, or α-hydroxyvaleric acid. The production process therefor is not particularly restricted, inclusive of fermentation process, synthesis process, etc. This is because an industrially supplied hydroxycarboxylic acid (aqueous solution) is inevitably accompanied with commingling of impurities regardless of any process through which it is produced. Among the hydroxycarboxylic acids, glycolic acid (boiling point under normal pressure: ca. 170° C.) and lactic acid (boiling point under normal pressure: ca. 210° C.) are preferred, and glycolic acid is particularly suitable to be processed by the purification process of the present invention since it has a strong inclination of polycondensation under heating.

Hereinbelow, the present invention is described in further detail with primary reference to application to glycolic acid, that is a preferred embodiment of the present invention. In the following description, "%" and "ppm" are by weight unless otherwise noted specifically.

[Process for Purifying Hydroxycarboxylic Acid by Distillation]

<Purification of Glycolic Acid>

(Starting Hydroxycarboxylic Acid Solution)

A hydroxycarboxylic acid starting material forming a distillation mother liquid together with a high-boiling point hydroxy compound added thereto in the present invention, has been generally diluted with a solvent. The diluting solvent can be an arbitrary solvent that is miscible with the hydroxycarboxylic acid, but is generally water in connection with the commercial process for production of hydroxycarboxylic acid.

Here is principally explained an embodiment of processing, as a starting liquid, a 70% technical-grade aqueous solution of glycolic acid (hereinafter sometimes referred to as "GA") containing ca. 1 wt. % (0.93%) of di-glycolic acid (sometimes referred to as "di-GA") as a representative impurity, and as other impurities, methoxy acetic acid 2.90%, formic acid 0.96%, $NH_4$ 23 ppm, Na 6 ppm, Ca 14 ppm, Mg 5 ppm and $SO_4$ 74 ppm.

GA aqueous solution as described above may be used as it is as a starting material for distillation or may be diluted with water, as desired, for suppressing the polycondensation velocity. However, as the degree of dilution becomes larger, a larger amount of water is distilled out together with GA, and this is not desirable from the viewpoint of thermal efficiency. The total concentration of GA and GA dimer in a GA aqueous solution used as a distillation starting material is generally ca. 2-90%, preferably ca. 10-70%, further preferably ca. 20-50%.

In the present invention, a high-boiling point hydroxy compound is added as a principal means for suppressing the polycondensation possibly caused by subjecting a GA aqueous solution at a concentration as mentioned above directly as the mother liquid to distillation under heating.

(High-Boiling Point Hydroxy Compound)

The high-boiling point hydroxy compound added as a polycondensation suppressing agent to the distillation mother liquid in the present invention, comprises at least one species selected from the group consisting of alcohols and phenols having a boiling point higher than GA (or an objective hydroxycarboxylic acid to be purified by distillation) and, for this purpose, should preferably have a boiling point higher than 170° C., particularly 200° C. or above.

As the high-boiling point hydroxy compound, arbitrary alcohols or phenols having a boiling point for suppressing the distilling-out and an OH group. Specific examples thereof may include: monohydric alcohols, such as 1-octadecanol, diphenyl methanol, dodecanol, 1-tridecanol, 3-phenyl-1-propanol and 1-hexadecanol, or phenols, such as 1-naphthol, 2-naphthol and pyrodecanol; in addition, alkylene glycols having 2OH groups and also a linear or branched alkylene group, such as ethylene glycol, propylene glycol, butylene glycol, hexane diol and decanediol, and (poly)alkylene glycols having two OH groups and also at least one linear or branched oxyalkylene group inclusive of polyalkylene glycol, such as diethylene glycol, propylene glycol, butylene glycol, polyethylene glycol, polypropylene glycol and polybutylene glycol; and (poly)alkylene glycol monoalkyl ethers formed by converting one of the two OH groups of the (poly)alkylene glycols into an alkyl ether moiety. Among these, high-boiling point alcohols are preferably used, and (poly)alkylene glycol mono-alkyl ethers are particularly preferred.

Incidentally, these high-boiling point hydroxy compounds may effectively function as a compatibilizer for improving mutual solubility between an oligomer and a polar organic solvent to stabilize the de-polymerization system in the process for producing a cyclic ester according to the present invention (i.e., a process for producing a cyclic ester by de-polymerization of an oligomer in mixture with a polar organic solvent, which oligomer has been obtained by polycondensation of a hydroxycarboxylic acid purified by the present invention), and the distilling-out thereof together with the hydroxycarboxylic acid need not be strictly suppressed as far as it is used for purification of a hydroxycarboxylic acid which is used as a starting material in the process for producing a cyclic ester according to the present invention.

The high-boiling point hydroxy compound is added for the purpose of suppressing the polycondensation of hydroxycarboxylic acid in the distillation mother liquid. The minimum amount thereof is an amount effective for obviating the failure of continuation of distillation due to solidification of the distillation mother liquid, and the amount is ca. 0.5 mol % in terms of a concentration in the mother liquid (i.e., the amount of alcoholic (or phenolic) OH with respect to the total OH of GA and the high-boiling point hydroxy compound). However, a larger amount is preferred for lowering the viscosity of the mother liquid and the distillation temperature. The upper limit is determined principally from the viewpoint of distillation cost, and at an OH concentration exceeding 50 mol %, the polycondensation suppression effect in saturated. Accordingly, the used amount of the high-boiling point hydroxy compound is in the range of 0.5-50 mol %, preferably 10-40 mol %, particularly 20-30 mol %, in terms of an OH concentration in the mother liquid.

As a result of the dilution with the high-boiling point hydroxy compound, the total concentration of the hydroxycarboxylic acid and oligomers including dimer thereof in the mother liquid is ordinary ca. 30-80%, preferably ca. 35-70 wt. %.

As for the distillation temperature, the lower limit thereof is determined from the viewpoint of providing a substantial distillation speed and can be lowered under a reduced pressure. As for the upper limit, heating in excess of 200° C. is not desirable since it increases the speed of generation of di-GA that is an ether-bonded product of GA due to side reaction.

Accordingly, for the purpose of the present invention, it is preferred to use a distillation temperature of ca. 50-200° C., more preferably ca. 100-200° C., particularly ca. 120-200° C., under normal pressure or a reduced pressure down to ca. 1 kPa.

The distillation may be performed batchwise or (semi-) continuously by using a distillation apparatus of vessel-type (evaporation still) or tower-type. From the viewpoint of purification of GA by separation from heavy impurities such as di-GA and heavy matter such as GA oligomer formed due to polycondensation, batchwise simple distillation may be sufficient, but from the viewpoint of effective utilization of the apparatus, it is preferred to adopt a semi-continuous scheme wherein at least the feed is made continuous. As heavy impurities including di-GA to be removed are accumulated in the mother liquid at the apparatus bottom, it is also preferred to withdraw the mother liquid from the apparatus bottom to increase the time of continuation of the semi-continuous operation. Alternatively, it is of course possible to effect a continuous operation by continuous withdrawal of small quantities while the control system may be somewhat complicated.

Further, while the high-boiling point hydroxy compound used in the present invention has an effect of preventing the accumulation of GA oligomers including GA dimer in the distillation mother liquid in addition to the effect of preventing the polycondensation of GA, the GA oligomers including GA dimer, as different from di-GA of ether-type, do not act as harmful impurities even if distilled together with GA, for the purpose of production of glycolide and polyglycolic acid through GA oligomer (more generally, production of cyclic ester and polyhydroxycarboxylic acid through hydroxycarboxylic acid oligomer) described hereinafter.

Incidentally, simple distillation is sufficient for the purpose of separation of heavy matter as principal impurities, it is possible to adopt means or schemes, as desired, of refluxing for improving the rectification efficiency, or a multi-stage distiller for allowing the withdrawal of GA from a middle stage to remove light impurities, such as methoxy acetic acid, formic acid and oxalic acid. Further, in the batchwise operation, it is easily practiced to once perform distillation at a temperature below the GA distillation temperature so as to remove light impurities in advance. Further, even if such light impurities remain in GA, they are removed together with water during the oligomer production, so that they are not substantially contained in the GA oligomer.

(Application to Other Hydroxycarboxylic Acids)

In the above, the process for purification of hydroxycarboxylic acid by distillation according to the present invention has been described with reference to a preferred embodiment of application to glycolic acid, the applicability of the process to other hydroxycarboxylic acids having thermal polycondensability may be easily understood by one of ordinary skill in the art. For example, it can be applied to lactic acid, etc. Some points may be different such that as lactic acid has a boiling point of ca. 220° C., it is necessary to add an alcohol or phenol having a higher boiling point, whereas the other conditions may be applicable similarly thereto.

(Process for Production of a Cyclic Ester)

In the process for producing a cyclic ester according to the present invention, an aqueous solution of a hydroxycarboxylic acid purified through the above-mentioned process is polycondensed, as it is or after dilution or condensation for adjustment of the concentration, into an oligomer of the hydroxycarboxylic acid, and the oligomer is de-polymerized to form a cyclic ester that is a dimer of the hydroxycarboxylic acid. The co-presence of a high-boiling point hydroxy compound entrained with the hydroxycarboxylic acid from the distillation system does not exert any adverse effects to the formation of hydroxycarboxylic acid oligomer by polycondensation.

For example, in the case where the hydroxycarboxylic acid is glycolic acid, the glycolic acid aqueous solution purified and recovered through the above-mentioned process may be adjusted to a concentration of at most 70% for the convenience of storage and handling, and the glycolic acid aqueous solution may be further condensed and polycondensed to recover glycolic acid oligomer, which may be further decomposed according to a process described in WO2002/083661A to recover glycolide (i.e., cyclic dimer ester of glycolic acid) useful as a starting material for producing polyglycolic acid. More specifically, the above-mentioned WO2002/083661A (the entire disclosure of which is intended to be incorporated herein by reference) discloses a glycolide production process including a step of depolymerization by heating of a glycolic acid oligomer recovered in the above-described manner, wherein:

a depolymerization reaction is carried out through the following steps (i) to (iv):

step (i) of heating a depolymerization reaction system comprising a glycolic acid oligomer or a glycolic acid oligomer plus a polar organic solvent to depolymerize the glycolic acid oligomer into glycolide, step (ii) of distilling the glycolide formed by depolymerization or the glycolide and polar organic solvent out of the depolymerization reaction system, step (iii) of recovering the glycolide from distillates obtained by distillation, and step (iv) of charging the glycolic acid oligomer or the glycolic acid oligomer and polar organic solvent continuously or intermittently into the depolymerization reaction system, in which:

(v) during the depolymerization reaction, a compound (A) having an alcoholic hydroxyl group is permitted to exist in the depolymerization reaction system, provided that the amount of the compound (A) in the depolymerization reaction system is controlled such that the alcoholic hydroxyl group amount of said compound (A) is kept at 0.5 equivalent or greater with respect to the total carboxyl group amount of an organic acid (B) comprising diglycolic acid, methoxy acetic acid and oxalic acid formed upon hydrolysis of the depolymerization reaction system under alkaline conditions.

In the above-described glycolide production process, a polar organic solvent is used as a solvent for the de-polymerization reaction and also plays a role of being co-distilled with the glycolide and accompanied with the glycolide to outside the de-polymerization system. The polar organic solvent may preferably have a boiling point in the range of 230-450° C. Further, the polar organic solvent may preferably have a molecular weight in the range of 150-450.

As the polar organic solvent, aromatic dicarboxylic acid diesters, aliphatic dicarboxylic acid diesters and polyalkylene glycol diethers may be used, and among them, polyalkylene glycol diethers are preferably used.

As the compound (A) having an alcoholic hydroxyl group used in the above-mentioned glycolide production process, the high-boiling point hydroxy compound used in the process for distillation purification of hydroxycarboxylic acid according to the present invention may be effectively used as it is. In the de-polymerization system, the high-boiling point hydroxy compound plays a function of improving the mutual solubility between the glycolic acid oligomer and the polar organic solvent to stabilize the de-polymerization system. A (poly)alkylene glycol monoalkyl ether is particularly preferred.

(Process for Production of a Polyhydroxycarboxylic Acid)

A cyclic ester obtained in the above-described manner is generally known to be a good starting material for producing a polyhydroxycarboxylic acid through ring-opening polymerization thereof.

For the ring-opening polymerization of a cyclic ester, it is preferred to adopt a process of melting the cyclic ester under heating in the presence of a catalyst, and then subjecting the cyclic ester in a molten state to ring-opening polymerization. The polymerization process is a bulk-state ring-opening polymerization process. The ring-opening polymerization of a cyclic ester in a molten state may be effected batch-wise or continuously by using a reaction vessel, or a tube-type, column-type or extruder-type reaction apparatus. It is generally preferred to adopt a method of bulk-state ring-opening polymerization in a polymerization vessel. For example, when glycolide is heated, the glycolide forms a molten liquid and is polymerized on continued heating to form a polymer. In case where the polymerization temperature is below a crystallization temperature of the solid polymer, the polymer is precipitated in the course of polymerization to finally obtain a solid polymer. The polymerization time can vary depending on the ring-opening polymerization process and polymerization temperature but may ordinarily be 10 min.-100 hours, preferably 30 min.-50 hours, further preferably 1-30 hours, in the case of ring-opening polymerization in a vessel. The polymerization conversion is generally at least 95%, preferably 98% or higher, further preferably 99% or higher. It is most preferred to effect a full conversion (a polymerization conversion of substantially 100%) in order to minimize the remaining of unreacted monomer and increase the production efficiency.

Further, it is also preferred to adopt a process of transferring the cyclic ester in a molten state into a polymerization apparatus comprising a plurality of tubes (preferably having both ends that can be opened or closed) and proceeding with the ring-opening polymerization in an airtight state in each tube; or a process of proceeding the ring-opening polymerization of the cyclic ester in a molten state in a reaction vessel equipped with a stirrer, taking out a purified polymer, once cooling and solidifying the polymer and further continuing solid-state polymerization of the polymer at a temperature below the melting point of the polymer. These polymerization processes can be effected either batch-wise or in a continuous manner. In any process, by controlling the polymerization temperature in an airtight state (i.e., in a reaction system not including a gaseous phase), it is possible to produce a polymer having-objective properties, such as molecular weight and melt-viscosity stably and at a good reproducibility.

In effecting the above-mentioned bulk-state ring-opening polymerization of cyclic ester, it is preferred to subject a cyclic ester containing water and/or alcohol as an initiator or/and a molecular weight-regulating agent with a total proton concentration in the cyclic ester as a controlling parameter.

The details of such a process for producing a polyhydroxycarboxylic acid are disclosed in, e.g., WO2005/035623A1, WO2005/044894A1 and WO2007/086563A1, and the disclosure of these documents are incorporated herein by reference.

EXAMPLES

Hereinbelow, the process for purifying a hydroxycarboxylic acid by distillation according to the present invention will be described more specifically based on Examples (experimental examples).

Incidentally, the contents of GA and impurities, such as di-GA, in the following Examples are based on the values measured according to the following methods, and GA recovery yields are also based on the results.

<Methods for Quantitative Determination of GA (and GA Dimer), di-GA, Methoxy Acetic Acid and Formic Acid>

Analyzer: HPLC (high performance liquid chromatography) apparatus ("SCL-6B", made by K.K. Shimadzu Seisakusho)

Detector: UV (wavelength: 210 nm)

Column: Two columns of "Inertsil ODS-3V" (made by GL Science Co.) connected in series Column temperature: 40° C.

Elution liquid: A solution of 26.6 g of phosphoric acid and 11.5 g of ammonium dihydrogen-phosphate in 1 L of pure water.

Flow rate: 0.7 ml/min.

A sample is accurately weighed at 1 g, and 0.6 g of sodium hydroxide is added thereto, followed by dissolution in 20 ml of pure water and 30 min. of standing at room temperature. After lapse of the 30 min., 1 ml of hydrochloric acid is added thereto for adjustment to an acidity, and the solution is messed up to 50 ml, followed by injection of 20 μl of the solution to the HPLC. Corresponding standard substances are respectively adjusted to prepare calibration curves, and the concentration of the respective components are calculated based on areal ratios. (Incidentally, according to the above analysis method, GA dimer is hydrolyzed with sodium hydroxide to be measured as a portion of GA.)

<Quantitative Determination of Metals, Such as Na, Ca, Mg, Etc.>

Measured by ICP (inductively coupled plasma) emission spectrometry. More specifically, 3 ml of conc. sulfuric acid and 5 ml of nitric acid are added to 1 g of a sample to decompose the sample in a wet state, and the solution is subjected to ICP spectroscopy for the quantitative determination.

<Quantitative Determination of $SO_4$, $NH_4$>

A sample solution is subjected to determination by ion chromatography under the following conditions Apparatus: For $SO_4$, "DX-320J", made by Dionex Corp. For $NH_4$, "DX-500", made by Dionex Corp.

Column: "AS-11", for $SO_4$, "CS-12A" for $NH_4$,

Measurement temperature: 35° C. for $SO_4$, room temperature for $NH_4$

Elution liquid: 10 mM-NaOH for $SO_4$, 20 mM-methanesulfonic acid.

Flow rate: 1.0 ml/min.

Injection volume: 25 μl

Detection: Electroconductivity measurement.

Example

A distillation experiment was performed by using an apparatus as illustrated in FIG. 1.

The starting materials included 200 g of industrial-grade GA aqueous solution (made by DuPont) containing 66.32% of GA (and dimer thereof) and, as impurities, 0.93% of di-GA (and further 2.90% of methoxy acetic acid, 0.90% of formic acid, 23 ppm of $NH_4$, 6 ppm of Na, 14 ppm of Ca, 5 ppm of Mg and 74 ppm of $SO_4$), and 200 g of polyoxyethylene-2-ethylhexyl ether ("Newcol 1006", made by Nippon Nyuhkazai K.K.; boiling point: above 300° C.), which were charged as an initial mother liquid into an evaporation still (distillation vessel) having an inner volume of ca. 0.5 liter and heated to 140° C. under a reduced pressure of 3 kPa·abs., thereby cutting off (removing) 81.2 g of an initial distillate. Then, a feed liquid separately formed in a starting material vessel by diluting the above-mentioned starting material GA aqueous solution with water to provide concentrations at 25.73% of GA (and dimer thereof) and, as impurities, 0.35% of di-GA (and further 1.11% of methoxy acetic acid, 0.37% of formic acid, 9 ppm of $NH_4$, 2 ppm of Na, 5 ppm of Ca, 2 ppm of Mg and 28 ppm of $SO_4$), was fed at a substantially constant flow rate. Thereafter, 27 hours of distillation run was performed while regulating the thermal input to and output from the evaporation still so as to provide identical feed liquid and distilled liquid rates, thereby processing totally 687.9 g of the feed. The temperature in the distillation still was 141.8° C. at the time of the feed start and 143.4° C. after the 27 hours.

Even after the 27 hours of run, the mother liquid was not solidified, thus allowing the continuation of distillation.

The initial distillate in an amount of 81.2 g exhibited a GA concentration of 6.57% and no detectable impurities.

The distilled liquid after cutting off the initial distillate was weighed at 748.4 g and contained 27.66% of GA (and dimer thereof) and, as impurities, 0.03% of di-GA (and further 0.40% of methoxy acetic acid 0.35% of formic acid, 3 ppm of $NH_4$ with no detectable amounts of Na, Ca, Mg or $SO_4$). Further, GA yield including the initial distillate was calculated as (distilled GA)/(initially charged GA+fed GA)= (81.2×0.0657+784.8×0.2766)/(200×0.6632+687.9× 0.2537)= 0.6913, i.e., 69.13%. Thus, even at a high yield of ca 70%, the impurity concentration was suppressed low, particularly at 0.03% of di-GA (corresponding to 0.11% of GA), thus exhibiting a remarkable purification effect compared with the concentration (1.40% of GA) in the feed liquid.

Comparative Example

A distillation experiment was performed in a similar manner as in the above Example except for using an apparatus obtained by re-modeling the apparatus shown in FIG. 1 so that the total condenser was used as a partial condenser and a total condenser for condensing evaporated water was placed thereafter, and the feed liquid was diluted to a higher dilution ratio without using the high-boiling point hydroxy compound.

More specifically, a starting material consisting of 400 g of the same industrial-grade glycolic acid aqueous solution (made by DuPont) alone was charged as the initial mother liquid into the evaporation still (distillation vessel) having an inner volume of ca. 0.5 liter and heated to 140° C. under a reduced pressure of 3 kPa·abs. Then, the inner pressure in the still was restored to normal pressure, and a feed liquid separately formed in the starting material vessel by diluting the above-mentioned starting GA aqueous solution with water to provide concentrations at 4.00% of GA (and dimer thereof) and, as impurities, 0.05% of di-GA (and further 0.17% of methoxy acetic acid, 0.06% of formic acid, 1 ppm of $NH_4$, no detectable amounts of Na, Ca or Mg, and 4 ppm of $SO_4$), was fed at a substantially constant flow rate. Thereafter, 25 hours of distillation run was performed while regulating the thermal input to and output from the evaporation still so as to provide identical feed liquid and distilled liquid rates, thereby processing totally 3403.6 g of the feed. The temperature in the distillation still was 139° C. at the time of the feed start and 140° C. after the 25 hours.

Even after the 25 hours of run, the mother liquid was not solidified, thus allowing the continuation of distillation.

The distilled liquid recovered by the partial condensation was weighed at 578.7 g and contained 31.15% of GA (and dimer thereof and, as impurities, 0.03% of di-GA (and further 0.35% of methoxy acetic acid 0.36% of formic acid, 4 ppm of $NH_4$ with no detectable amounts of Na, Ca, Mg or $SO_4$). Further, GA yield in the distillation was calculated as (distilled GA)/(initially charged GA+fed GA)=(578.7×0.3115)/ (400×0.6632+3403.6×0.04)=0.4491, i.e., 44.91%. Thus, the concentration of impurity di-GA was suppressed low, at 0.03% of di-GA (corresponding to 0.10% of GA), thus exhibiting a remarkable purification effect compared with the concentration (1.40% of GA) in the feed liquid, whereas the GA yield was low and a large amount of evaporated water had to be treated while the continuation of the distillation was possible.

As the above-mentioned distillation under normal pressure was considered to have resulted in a slow vaporization speed and a low concentration of GA, the distillation under a reduced pressure similarly as in Example was tried, whereas it was impossible to retain water in the mother liquid and the mother liquid was solidified due to polycondensation so that the continuation of the distillation became impossible.

Industrial Applicability

As is understood from the results of the above Example (experimental example), in the purification of a hydroxycarboxylic acid from an industrial-grade hydroxycarboxylic acid (aqueous solution) to which it has been difficult to apply distillation due to its thermal polycondensability, the present invention has made possible the purification of a hydroxycarboxylic acid in a stable distillation system by causing the distillation mother liquid to contain a high-boiling point hydroxy compound to suppress the polycondensation of the hydroxycarboxylic acid. Further, according to the present invention, there are further provided a process for producing a cyclic ester and a process for producing a polyhydroxycarboxylic acid from the thus-purified hydroxycarboxylic acid as a starting material. Further, the thus-purified hydroxycarboxylic acid such as glycolic acid obtained through the process of the present invention can be used not only as a starting material for production of a polyhydroxycarboxylic acid but also as a starting material for chemical synthesis products for which an equal or lower level of purity is sufficient and, if necessary, as a starting material for another purification method for obtaining a higher purity of hydroxycarboxylic acid, e.g., crystallization method of Patent document 1 or 2 while one-pass yield thereof may be low.

The invention claimed is:

1. A process for purification of glycolic acid by distillation, comprising: adding a high-boiling point hydroxy compound comprising at least one species selected from the group consisting of alcohols and phenols having a higher boiling point than glycolic acid to an aqueous solution of glycolic acid containing impurities to form a mixture solution, and distilling the mixture solution to distil out the glycolic acid and water together to form an aqueous solution of glycolic acid with reduced impurities, while leaving the high-boiling point hydroxyl compound and the impurities as distillation residues.

2. A process according to claim 1, wherein in the mixture solution, the high-boiling point hydroxy compound provides an amount of OH which is 0.5-50% of a total amount of OH provided by the glycolic acid and the high-boiling point hydroxy compound.

3. A process according to claim 1, wherein the high-boiling point hydroxy compound has a boiling point in excess of 170° C.

4. A process for producing glycolide, comprising:
polycondensing a glycolic acid purified through a process according to claim 1 in an aqueous solution to form an oligomer thereof, and then de-polymerizing the oligomer in mixture with a polar organic solvent to obtain a glycolide.

5. A production process according to claim 4, wherein the de-polymerization of the glycolic acid is performed in mixture with the polar organic solvent and the high-boiling point hydroxy compound.

6. A process for producing polyglycolic acid, comprising: subjecting the glycolide produced through a process according to claim 4 to ring-opening polymerization.

* * * * *